United States Patent [19]

Stuart

[11] 4,036,961
[45] July 19, 1977

[54] PHARMACEUTICAL COMPOSITIONS CONTAINING PTERIDINES

[75] Inventor: Alexander Stuart, Bromley, England

[73] Assignee: Burroughs Wellcome Co., Research Triangle Park, N.C.

[21] Appl. No.: 622,226

[22] Filed: Oct. 14, 1975

Related U.S. Application Data

[62] Division of Ser. No. 382,715, July 26, 1973, Pat. No. 3,939,160.

[30] Foreign Application Priority Data

Aug. 1, 1972 United Kingdom ............... 35815/72
Feb. 1, 1973 United Kingdom ............... 5189/73

[51] Int. Cl.² ...................... A01N 9/22; A61K 31/505
[52] U.S. Cl. .................................................. 424/251
[58] Field of Search .................. 424/251; 260/251.5

[56] References Cited

U.S. PATENT DOCUMENTS

| | | | |
|---|---|---|---|
| 2,584,538 | 2/1952 | Boothe | 260/251.5 |
| 3,635,978 | 1/1972 | Wood et al. | 260/251.5 X |
| 3,810,893 | 5/1974 | Wood et al. | 260/251.5 |

*Primary Examiner*—Allen J. Robinson
*Attorney, Agent, or Firm*—Dike, Bronstein

[57] ABSTRACT

Pharmaceutical compositions containing the pteridines of formula (I),

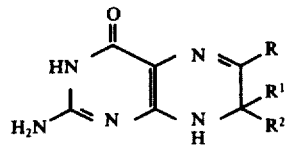

wherein R is a lower alkyl group, substituted with one or more halogen atoms, and $R^1$ and $R^2$ are the same or different and each is a lower alkyl group or $R^1$ and $R^2$, together with the carbon atom in the pteridine ring structure, form a spirocycloalkyl ring system having 4 to 6 carbon atoms outside the pteridine ring structure.

The above compositions have bacteriostatic activity.

16 Claims, No Drawings

PHARMACEUTICAL COMPOSITIONS CONTAINING PTERIDINES

This is a division of application Ser. No. 382,715, filed on July 26, 1973, now U.S. Pat. No. 3,939,160 issued Feb. 17, 1976.

The present invention relates to derivatives of pteridine, their chemical synthesis and pharmaceutical formulations containing them. The specification also describes compositions and pharmaceutical formulation comprising these pteridines in combinations which are useful in the treatment of microbial infections.

It is already established that the compounds 2-amino-4-hydroxy-6-hydroxymethyl-7,7-dimethyl-7,8-dihydropteridine and 2-amino-4-hydroxy-6-methyl-7,7-dimethyl-7,8-dihydropteridine or their tautomers or pharmaceutically acceptable salts thereof, have bacteriostatic activity, being particularly effective against Cl. perfringens and Derm. dermatonomous, as disclosed in the specifications of British Pat. No. 1303171 and Application No. 36289/70 (Belgian Pat. No. 770,577).

It has now been found that the novel pteridines represented by the following formula (I) or their tautomers or pharmaceutically acceptable salts thereof,

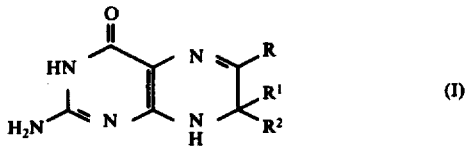

wherein R is a lower alkyl group, substituted with 1 or more halogen atoms, and R¹ and R² are the same or different and each is a lower alkyl group or R¹ and R², together with the carbon atom in the pteridine ring structure, form a spirocycloalkyl ring system having 4 to 6 carbon atoms outside the pteridine ring structure, are also useful as antagonists of microbial metabolism.

As used herein and throughout the specification, the term "lower alkyl group" refers to a straight or branched chain alkyl group having 1 to 4 carbon atoms.

Those compounds wherein R is a lower alkyl group, desirably a methyl group, substituted on the carbon atom adjacent the pteridine ring structure are preferred. Most preferably this alkyl group is mono- or di- substituted, conveniently with bromine atoms. Furthermore R¹ and R² are preferably lower alkyl groups and in particular they are the same and both methyl groups. The compounds 2-amino-4-hydroxy-6-bromomethyl-7,7-dimethyl-7,8-dihydropteridine and the 6-dibromomethyl analogue are especially preferred.

According to the present invention, therefore, there are provided in one aspect the novel compounds of formula (I).

The above compounds and their salts inhibit one of the enzymes involved in the biosynthesis of dihydrofolic acid, namely hydroxymethyldihydropteridine pyrophosphokinase, which is essential to the growth of microorganisms, for instance bacteria. They can thus be used in in vitro pharmacological investigations in clinical and diagnostic tests establishing, for instance, the properties of bacteria. When used as bacteriostats they may be present in a concentration of 50 to 500, in particular 110 to 180 mg of base/ml of the solution in which the organism grows in the absence of a compound. A further use of the compounds, when in solution, is in the treatment of wounds, for example after surgery, to prevent the growth of bacteria. Moreover the compounds of formula (I) and their salts manifest unexpectedly low toxicity in mammals or birds e.g. poultry, which makes them particularly suitable for application against microbial infections in such hosts under circumstances hereinbelow described.

Tetrahydrofolate co-factors are essential metabolites in all cells for the biosynthesis of purines, thymidylic acid, serine and several other biologically important compounds. Most of these co-factors are 1-carbon adducts of tetrahydrofolic acid. The ultimate source of these for higher animals and man is food, containing preformed folates usually in the form of vitamins.

In micoorganisms, the co-factors are synthesised from simpler chemicals. Generally the bio-synthetic process first provides 'dihydropteridine' (Pt), i.e. 2-amino-4-hydroxymethyl-7, 8-dihydropteridine (HMPt) pyrophosphate ester, from its immediate precursor HMPt in the presence of the enzyme hydroxymethyldihydropteridine pyrophosphokinase (HMPPS). Pt then condenses with p-aminobenzoic acid (pAB) in the presence of the enzyme dihydropteroate synthetase to form dihydropteroic acid (DPtA). This intermediate further condenses with a glutamate to form dihydrofolic acid (DFA or 'folate') which is then enzymatically reduced to provide the essential tetrahydrofolate in, for instance, bacteria and other micro-organisms.

The provision of the 'folate' from the basic building blocks, i.e. pteridine, pAB, and glutamate, and the further conversion of this into the tetrahydrofolate is known to be inhibited in two different ways. For instance sulphonamides displace pAB in the above reaction scheme. Because of their close structural resemblance to pAB, sulphamides or similar other 'competitors' enter the biosynthesis and prevent the formation of DPtA, and the DFA, and are therefore antimetabolites for the metabolite pAB. It is also known that compounds which are 'inhibitors' of the enzyme dihydrofolic acid reductase block the synthetic stop leading to tetrahydrofolate. A considerable number of pyrimidine derivatives show substantial anti-microbial properties on the basis of such blockage.

It was established later that such inhibitors may act synergistically with sulphomamides, i.e. there can be a sequential double blockade and a strong mutual potentiation of the anti-bacterial effects of the two materials. The range of anti-microbial action exerted by such combinations is considerably wider than that expected from the activity of either drug, and organisms which are only marginally sensitive to the individual agents become very sensitive to the combinations.

It was also suggested hypothetically that antimetabolites to Pt could inhibit the biosynthesis of DPtA (and DFA) (cf. Hitchings and Burchall *Advances in Enzymology,* 27, 417–468 (1965)) but compounds so far tested for the purpose have been disappointing, being either inactive or too toxic or sometimes both (cf. the compounds described in British Pat. Nos. 981,506 and 987,916).

It has been established that, for antimicrobial purposes, it is a prerequisite for the effective antagonism of Pt that the compound should be an inhibitor of MHPPS without also acting as an antimetabolite to the dihydropteridine that serves as a cofactor for the hydroxylation of phenylalanine and tyrosine, precursors of the catecholamines, such as norepinephrine, that have important actions as regulators of cardiovascular systems. Such an antimetabolic effect could lead to prohibitive toxicity to avian or mammalian species, which are normally the hosts ineffected with the microbes.

It has now been found that the compounds of formula (I) and their salts fulfil the above requirements i.e. inhibition of HMPPS combined with low toxicity to host species, as demonstrated for instance in chicks and rats. These compounds not only inhibit the growth of microorganisms on their own, albeit to a limited extent with certain bacteria, such as *Staphylococcus aureus, Streptococcus pyogenes, Streptococcus baccalis, Escherichia coli, Slamonella typhi, Proteus vulgaris, Pseudomonas aerugenosa, Pasteurella multodica* among others, but have been found to act with a most remarkable synergistic effect when combined with a competitor of p-aminobenzoic acid, i.e. sulphonamides and similar compounds, or with selective inhibitors of dihydrofolic reductase, i.e. pyrimidines and related compounds, or with a combination of both of these types of antimicrobial agents. This potentiating effect of the compounds of formula (I) is the subject of co-pending cognate British Patent Application No. 36774/71.

In that application there is described and claimed a composition for testing or treating microbial systems or infections, comprising an effective potentiating amount of a compound of formula (I) in combination with an effective amount of a competitor or inhibitor, or both, as herein defined.

The microbial infections against which these combinations are effective are protozoal or bacteria infections caused by those microorganisms which synthesise at least a substantial part of their tetrahydrofolate co-factor requirements. More specifically these infecting microorganisms are those which adequately absorb the pharmaceutical combinations disclosed herein and further are those in which these combinations have a synergistic effect in interfering with the de novo synthesis of the required tetrahydrofolate co-factors. For example, the compositions described have been found to be useful in the treatment of infections caused by *Staphylococcus aureus, Pseudomonas aerugenosa* and *Pasteurella multocida.*

It has been found specifically that, when compounds of formula (I) are combined with an amount of the competitor and/or the inhibitor which is not ordinarily sufficient to be effective as an antimicrobial agent in its own right, the combination of a compound of formula (I) with this normally ineffective amount of the competitor and/or the inhibitor provides a composition which in totality acts as an effective antimicrobial agent. This is especially notable when the amount of the compound of formula (I) is so low that it has substantially no microbial effect at the particular levle, yet in the combination the potentiation is marked, in some instances very marked. Thus by using an effective potentiating amount of compound of formula (I) together with the competitor and/or the inhibitor, it is now possible to reduce significantly the amount of the competitor and/or the inhibitor required to inhibit the growth of these bacteria.

In accordance with the above therefore, the term "an effective amount" used in conjunction with the terms a dihydrofolic reductase 'inhibitor' and a para-aminobenzoic acid 'competitor' means either (a) an amount of the 'inhibitor' or 'competitor' which is effective to a degree as an antimicrobial agent in its own right but which is potentiated by the use of a compound of formula (I) or (b) an amount of the 'inhibitor' or 'competitor' which is ineffective as an antimicrobial agent but which when combined with a compound of formula (I) provides a composition which is an effective antimicrobial agent. An "effective potentiating amount" means an amount of the compound of formula (I) which increases the activity of an inhibitor and/or a competitor so as to provide an improved or adequate effectiveness for the whole combination.

It should be emphasised that the inhibition of the biosynthetic processes by such means could be termed as competitive antagonism in all three instances, and there might be potentiation between all three types of agents. The terms 'inhibitor', 'competitor', and 'potentiation' by a compound of formula (I) are arbitrary and should only serve as convenient names for the appropriate type of components in combination products described and claimed in the specification of the aforementioned cognate application.

The inhibiting activity against HMPPS of a selected compound of formula (I) can, for instance, be tested by monitoring the transfer of the terminal phosphate of adenosine triphosphate ATP-$\gamma$-$P^{32}$ to 'dihydropteridine'. It was found that the concentrations required for 50% inhibition of the formation of Pt ($IC_{50}$) in such tests are well correlated and within the margin of error obtained by other relevant tests in this respect, which measure the inhibition of either of the two enzymes involved in the formation of HMPt and DPtA. Such inhibition may, for instance, be easily and simply carried out by incubating an extract of *E. coli* with pAB-7-$C^{14}$, ATP, Mg and 'dihydropteridine'. The formation of the dihydropteroate-$C^{14}$ can be quantitatively assayed after separating the unreated pAB substrate, for instance by chromatography. It has been found that compounds possessing in such tests an $IC_{50}$ value of about 100$\mu$M or less, usually below 50$\mu$M represent compounds exerting a useful potentiating effect, provided their toxicity in the appropriate vertebrates is acceptable. Preferably the value is 25$\mu$M or less, such as in the range between 2 12$\mu$M. Generally a value below 7$\mu$M is desirable.

As explained above, for the purpose disclosed it is essential that the compound of formula (I) should not have a prohibitive toxicity to the mammalian or avian hosts' cardiovascular systems. While low toxicity is therefore an essential requirement, a therapeutic index incorporates both the activity and toxicity values pertinent to the present disclosure and could be used with advantage for selection of potentiating compounds of formula (I).

The therapeutic index is defined as the ratio of the maximum tolerated dose to the minimum effective dose and in most cases is preferably greater than 10, suitably at least 5 and in exceptional circumstances at least about 3 for humans, but possibly as low as 2 for animals.

Although the art is aware of many compounds which are known competitors of para-aminobenzoic acid and are antimicrobials, the sulphur compounds which are disclosed as antimicrobial agents from the top of page 994 to page 1007 of the Merck Index, 8th Edition, 1968 are presented by way of example only.

Of the known compounds which are competitors, the following sulphonamide compounds (or pharmaceutically acceptable salts thereof) are preferred for the purpose described.

sulphanilamide, sulphadiazine, sulphamethisazole, sulphamethizole, sulphapyridine, sulphathiazole, sulphamerazine, sulphamethazine, sulphisoxazole, sulphasoxine sulphasomidine, sulphachlorpyridazine, 2-(p-aminobenzene)-sulphonamido-3-methoxypyrazine(Kelfizina), α-amino-p-toluenesulphonamide, 5-sulphanilamido-2,4-dimethyl pyrimidine, 4-(N'-acetyl sulphanilamido-5,6-dimethoxy pyrimidine, 3-sulphanilamido-4,5-dimethyl isoxazole, 4-sulphanilamido-5-methoxy-6-decyloxy pyrimidine, sulphamonomethoxine, 4-p-(8-hydroxy-quinilinyl-4-azo)-phenyl sulphanilamido-5, 6-dimethoxy pyrimidine, sulphadimethoxine, sulphamethoxazole, sulphaquinoxaline, and p-(2 methyl-8-hydroxy-quinolinyl-(5)-azo)phenyl sulphanilamido-5,6-dimethoxy pyrimidine. Examples of a non-sulphonamide type of competitor are p-amino salicyclic acid (PAS) and p,p'-diaminodiphenylsulphone.

Similarly, although many compounds are known which inhibit dihydrofolic reductase and act as antimicrobial agents, the compounds disclosed in the following patents are presented by way of example of compounds suitable for use for the purpose disclosed.

U.S. Pat. Nos. 2,658,897; 2,767,183; 3,021,332; 2,937,284; 3,322,765; 2,909,522; 2,624,732; 2,579,259; 2,945,859; 2,576,939; 2,926,166; 2,697,710; 2,749,345; and 2,749,344.

The following inhibitors (or pharmaceutically acceptable salts thereof) are preferred for the combinations described, however:

2,4-diamino-6-ethyl-5-p-chlorophenylpyrimidine (pyrimethamine), 2,4-diamino-5-(3'4',5'-trimethoxybenzyl)-pyrimidine (trimethoprim), 2,4-diamino-5-(3'4'-dimethoxybenzyl) pyrimidine (diaveridine), 2,4-diamino-5-(2'-isopropyl-4'-chlorophenoxy) pyrimidine, 2,4-diamino-5-methyl-6-sec-butylpyrido (2,3-d) pyrimidine, 2,4-diamino-5-methyl-6-benzylpyrido(2,3-d) pyrimidine, 2,4-diamino-6-benzylpyrido(2,3-d) pyrimidine, 2,4-diamino-5-6-trimethylenequinazoline, 2,4-diamino-5,6-tetramethylenequinazoline, 2,4-diamino-5-(2',4'5'-trimethoxybenzyl) pyrimidine, 2,4-diamino-5-(2'-ethyl-4',5-dimethoxybenzyl) pyrimidine, 2,4-diamino-5-(2'-methyl-4',5'-dimethoxybenzyl) pyrimidine.

However, the most preferred combinations include those combining a compound of formula (I), especially those wherein R is a bromomethyl or dibromomethyl group and R¹ and R² are both methyl groups, with sulphadiazine, sulphamethoxazole, sulphadoxine or sulphaquinoxaline as competitors, or with trimethoprim, diaveridine or pyrimethamine as inhibitors. In view of possible synergistic advantages of using certain competitors and inhibitors in combination against particular diseases, and the potentiating effect of compounds of formula (I) on both of these types of antibacterial compounds, it has been preferred to formulate triple combinations, comprising a compound of formula (I) with one of the above-mentioned preferred competitors, and one of such inhibitors. For example, combinations of sulphadiazine/trimethoprim, sulphamethoxazole/trimethoprim, sulphadoxine/trimethoprim or sulphaquinoxaline-diaveridine. each together with a compound of formula (I), give improved effectiveness when compared with the components alone or with pairs of them.

The compounds of formula (I) either alone or together with the competitor and/or the inhibitor, may be presented in association with a carrier in pharmaceutical formulations suitable for parenteral, topical, rectal or oral administration. The formulations for oral or rectal administration are advantageously presented in discrete units, such as tablets, capsules, cachets, ampoules or suppositories, each containing a predetermined amount of each compound, but may also be presented as a powder, as granules, as a solution or suspension in an aqueous or non-aqueous liquid, or as an ointment or paste for topical administration. For parenteral use, the formulations incorporating an aqueous or non-aqueous liquid carrier must be sterile and be presented in sealed containers. The formulations may be made by any of the known methods and may include one or more of the following accessory ingredients:

diluents, solutes to render the solution isotonic with the blood, buffers, flavouring, binding, dispersing, surface-active, thickening, lubricating and coating materials, preservatives, bacteriostats, antioxidants, suppository and ointment bases, and any other acceptable excipients.

In another aspect of the present invention, therefore, there is provided a pharmaceutical formulation comprising a compound of formula (I) in combination with a pharmaceutically acceptable carrier. In yet another aspect the present invention provides a method of making a pharmaceutical formulation by admixing the compound of formula (I) with a carrier by known techniques. The specification of the afore-mentioned cognate application further discloses and claims a pharmaceutical formulation comprising a composition, as hereinbefore defined, together with a carrier, and its method of preparation, by admixing the composition with the carrier by known, techniques.

Formulations containing the compound of formula (I) in association with a competitor or an inhibitor may also be presented in the form of a kit, which comprises separately packaged units or dosages of these components with instructions for use in a combined form. The instructions may also specify the manner of administration and indications for which the formula is suitable.

The compounds of formula (I), either for use alone or in association with a competitor and/or inhibitor, and also the competitors and inhibitors, may be presented in the form of their pharmaceutically acceptable salts of a mineral or organic acid, for example hydrochloric acid, hydrobromic acid, sulphuric acid, acetic acid, citric acid, tartaric acid, lactic acid, maleic acid or salicylic acid, or, especially for the sulphonamide competitor, of a base, such as sodium hydroxide, potassium hydroxide, tetramethyl ammonium hydroxide or ammonia.

The ratios in which the therapeutically active compounds of formula (I) are utilized in the compositions described in this specification can be varied between wide limits. Depending on the nature and circumstance of use, the compositions may contain the compound of formula (I) with the competitor and/or the inhibitor in appropriate proportions and dosages. For instance, in cases of uses in vivo it is often desirable to maintain a certain proportion of components in the blood serum or tissue fluids, preferably for a prolonged period. Depending on the various absorption, discharge or decomposition rates of the components, the initial quantities and proportions of the ingredients of the formulation can be different from that aimed at in the tissues in vivo. The formulations and dosages recommended for the general treatment of a particular human or animal disease must be adjusted according to the particular requirements of the recipients of the disease, the known activities of the competitor or inhibitor component against the causative organism, the half life and the toxicity of the components in vivo, and other practical requirements.

For example the composition or pharmaceutical formulation may contain from about 1 to 30 parts by weight, preferably 5 to 15 parts, of the compound of formula (I), or an equivalent amount of a salt thereof, and 1 to 30 parts preferably 5 to 15 parts, of a competitor, or an equivalent amount of a salt thereof, and/or one part of an inhibitor, or an equivalent amount of a salt thereof.

Dosage will vary depending upon the infecting organism but under ordinary circumstances up to about 60 mg/kg each of a compound of formula (I) and competitor, and up to about 7.5 mg/kg of inhibitor, in combination, can be administered daily in several doses. The composition or pharmaceutical formulation can be administered to human patients in unit dosage forms which contain up to 750 mg of the compound of formula (I), and up to 750 mg of the competitor and/or up to 25 mg of the inhibitor. Preferably for adult dosages the amount of the compound of formula (I) would be about 200 mg, that of the competitor about 200 mg and/or that of the inhibitor about 25 mg.

The pharmaceutical formulation comprising the compound of formula (I) in combination with the competitor and/or the inhibitor is also usable in solution for irrigating wounds, for example after surgery, so as to prevent the growth of bacteria. For example, an antibacterial solution having the following preferred concentration of components may be used:

1–30 mg/ml of the compound of formula (I), 1–30 mg/ml of the competitor and/or 0.03–1 mg/ml of the inhibitor, in a pharmaceutically acceptable solvent, suitable for external use.

The potentiating effect of compounds of formula (I) can be demonstrated and utilized in vitro relatively easily for research and practical purposes. Such possiblities include diagnosis and the identification of the bacterial flora of individuals and the consequential selection of clinical treatment schedules.

The various combinations can be incorporated in porous discs (such as filter paper discs) or in Agar Nutrient or other media for bacterial growth for determining susceptibility. Those articles incorporating the compound of formula (I) with a competitor and/or an inhibitor compound may be distributed or sold to doctors, hospitals and clinics for the above purposes. A typical testing disc may be impregnated with a solution containing 5 to 50 µg/ml of a para-aminobenzoic acid competitor, 0.5 to 5 µg/ml of a dihydrofolic reductase inhibitor, and about 10 to 100 µg/ml of a compound of formula (I) in a medium comprising a mixture of an aqueous infusion and papain digest of horse muscle.

Furthermore, such pharmacological tests involving potentiated competitors or inhibitors may also be useful for the characteristics of bacteria according to their sensitivity and to their particular resistance for instance to a competitor when used alone, and such investigations involving a variety of formulations as described herein also form the basis of determining the compositions of selected formulations for general treatment purposes. The toxicity of compounds of formula (I) is generally considerably lower than that of the competitors or inhibitors commonly used, which may enable the clinician to maintain or increase the effectiveness of the antibacterial activity of the formulation with a concurrent increase of the therapeutic ratio or decrease in the toxic or side-effects of the medicament.

In addition to the above, compounds of formula (I) have been found to potentiate the activity of the aforementioned competitors and/or inhibitors against infections with microorganisms in domestic animals, including poultry, for example against *Pasteurella multocida* but especially against the protozoal disease coccidiosis. Such triple formulations comprising a compound of formula (I) together with a compound such as sulphaguinoxaline and an inhibitor such as diaveridine are effective in lower concentrations than the competitor or inhibitor components alone and possess an enhanced activity, being effective against all relevant Eimeria species causing this disease in poultry.

The compounds of formula (I) can, according to a further aspect of the present invention, be prepared by a method comprising the steps of reacting a compound of formula (II),

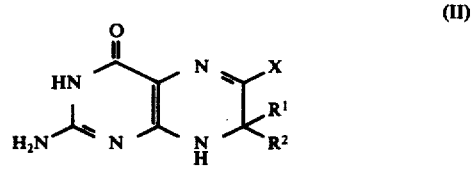

wherein $R^1$ and $R^2$ are as defined above and X is an alkyl, hydroxyalkyl or alkenyl group, with a halogenating agent, and isolating the compound so formed.

Conveniently halogenating agents in these respects include molecular halogens, hydrogen halides, phosphorus pentachloride, thionyl chloride and, for the preparation of bromo-substituted compounds, N-bromosuccinimide. The conversion of alkyl, hydroxyl or olefinic groups into halogeno substituted groups is well known in the literature and readily available to those skilled in the art. The selection of reaction conditions is governed by the nature of the reactants, but glacial acetic acid has been found to be a suitable solvent for the preparation of the preferred bromo-substituted compounds.

The compounds of formula (II) wherein X is an alkyl group or a hydroxyalkyl group may be prepared according to the procedure disclosed in the specification of copending British Patent Application No. 36289/70 (Belgian Pat. No. 770,577).

In this method a compound $R^1R^2C = CHX$ (VII), wherein $R^1$, $R^2$ and X are as defined above, undergoes an addition reaction with a nitrosyl halide, prepared in situ, and the resulting nitrosohalide (VI) is converted to the oxime (V) by reaction with ammonia solution. Reacting the oxime (V) with a 2-amino-4-halogeno-6-hydroxy-5-nitropyrimidine (IV) provides the pyrimidine ketoxime (III) which is then reductively cyclised to give the pteridine (II), as shown in the following sequence:

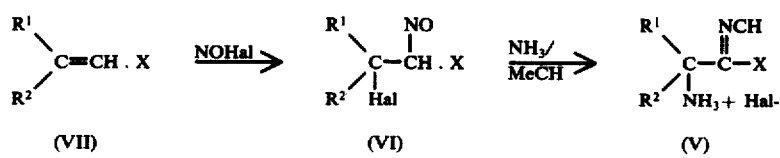

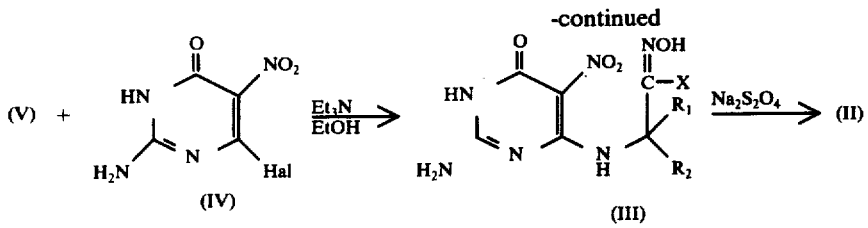

Those compounds of formula (II) wherein X contains a double bond may be prepared from the alkyl or hydroxyalkyl derivatives by standard reactions in the art. For example mild oxidation of a 6-hydroxyalkyl group to the corresponding aldehydic group followed by condensation with Wittig reagent, such as triethylphosphonoacetate or methylenetriphenyl-phosphorane produces an unsaturated linkage. Alternatively the 6-alkyl derivative may be condensed with an aldehyde under acid conditions to achieve the same result.

According to the present invention in further aspects there are also provided:

1. A compound of formula (I), whenever prepared from a compound of formula (II) by the method herein described.

2. A pharmaceutical formulation comprising a compound of formula (I) or a salt thereof in combination with a pharmaceutically acceptable carrier, whenever prepared by the method herein described.

The following Examples illustrate the invention but are in no way intended to limit the scope of the invention.

EXAMPLE 1

2-Amino-4-hydroxy-6-bromomethyl-7,7-dimethyl-7,8-dihydropteridine hydrobromide (I, R=CH$_2$Br, R$^1$=R$^2$=Me)

2-Amino-4-hydroxy-6-methyl-7,7-dimethyl-7,8-dihydropteridine (0.5 g) (II, X=Me, R$^1$=R$^2$=Me) was dissolved with gentle heating in glacial acetic acid (15 ml) and treated dropwise whilst stirring with bromine (0.125 ml) in glacial acetic acid (6 ml). The resulting solution turned a dark red colour and after 10 minutes a grey-green solid separated. After a further 10 minutes at room temperature this solid was filtered off and washed with ethanol and ether to give 0.7 g of product. The title compound (70% yield) was separated from small amounts of the starting material and the dibromomethyl derivative by thin layer chromatography.

EXAMPLE 2

2-Amino-4-hydroxy-6-dibromomethyl-7,7-dimethyl-7,8-dihydropteridine hydrobromide (I,R=CHBr$_2$, R$^1$=R$^2$=Me)

2-Amino-4-hydroxy-6-methyl-7,7-dimethyl-7,8-dihydropteridine (1 g) (II, X=Me, R$^1$=R$^2$=Me) was dissolved with gentle heating in glacial acetic acid (17 ml) and treated dropwise whilst stirring with bromine (0.5 ml) in glacial acetic acid (7 ml). The reaction mixture was stirred for a further 2 hours, during which time the colour had darkened considerably and a black-green tar had formed. The supernatant solvent was decanted and the tar treated with acetone (20 ml). Trituration followed by filtration gave a dark-green solid (1.5 g). The title compound (86% yield) was separated from small amounts of the starting material and the monobromomethyl derivative by thin layer chromatography.

EXAMPLE 3

2-Amino-4-hydroxy-6-1'-bromoethyl-7,7-di-n-propyl-7,8-dihydropteridine (R = CHBrCH$_3$,R$^1$ = R$^2$ = n-Pr)

To 2-amino-4-hydroxy-6-ethyl-7,7-di-n-propyl-7,8-dihydropteridine (0.277 g) (II, X=Et, R$^1$=R$^2$=n-Pr) in glacial acetic acid (3 ml) was added with stirring bromine (in slight excess) in acetic acid (2 ml) dropwise over 10 minutes. After a further 10 minutes orange crystals precipitated. After 30 minutes the precipitate was filtered off and washed well with dry ether. (Yield 170 mg; m.p. >300°). The title compound was separated from small amounts of the starting material and the dibromoethyl derivative by thin layer chromatography.

EXAMPLE 4

2-Amino-4-hydroxy-6-chloromethyl-7,7-dimethyl-7,8-dihydropteridine (R = CH$_2$Cl; R$^1$ = R$^2$ = Me)

A slight excess of chlorine was added with stirring to 2-amino-4-hydroxy-6-methyl-7,7-dimethyl-7,8-dihydropteridine, (II, X = Me, R$^1$=R$^2$=n-Pr) in glacial acetic acid, and the resulting precipitate was filtered off and washed with dry ether, and isolated analogously to the procedure described in Example 3.

EXAMPLE 5

Potential pteridine antagonists of formula (1) may be tested by investigating the inhibitory effect they impose on the enzymes responsible for the biosynthesis of dihydropteroic acid (DPtA), namely hydroxymethyldihydropteridine pyrophosphokinase (HMPPS), and dihydropteroate synthetase, hereinafter referred to as 'synthetase '. In the following reaction equations the compounds are referred to by their abbreviated forms defined on page 5 of the specification.

1. HMPS

2. Synthetase

(a) An assay for HMPPS was developed in which the transfer of the terminal phosphate of ATP-γ-P$^{32}$ to Pt could be monitored and correlated with the amount of inhibition of HMPPS by the compound under test.

The compound of formula (I) which was under test was incorporated into various formulations comprising metabolites and enzymes contained in test tubes, as indicated in TABLE 1.

The components of the mixture were as follows:

I—2-amino-4-hydroxy-6-hydroxymethyl-7,8-dihydropteridine (HMPt) in a concentration of 800 μM i.e. micromolar;

II—a source of HMPPS, obtained from an extract of E. coli and separated from 'synthetase' on Sephadex C-100, (Registered Trade Mark) according to the method of Richey and Brown in *J. Biol. Chem.* 244, 1582-1592 (1969)

III — 3mM ATP -γ-$P^{32}$.
IV — 0.10 M ATP neutralised (unlabelled).
V — 0.02M $MgCl_2.6H_2O$.
VI — 0.1 M $MgCl_2.6H_2O$.
VII — Source of HMPPS and 'synthetase'
VIII — the test compound in a concentration of $0.93 \times 10^{-3}$ M
IX — 0.4mM pAB-$C^{14}$ As shown in TABLE 1, tubes 1 to 9 all contain a source of HMPPS, labelled ATP and 0.02 M $MgCl_2.6H_2O$, tubes 2 to 9 containing in addition HMPt and tubes 4 to 9 further containing the test compound. Control tubes 10 to 12 include a source of both HMPPS and synthetase, unlabelled ATP, 0.1M $MgCl_2.6H_2O$ and labelled pAB.

Tubes 1 to 9 containing the amounts of components shown in the Table, were filled up to 200μl with distilled water, incubated for 60 minutes at 37° C and then chilled on ice. Dextrose (20μl containing 72.1 mg/ml) and hexokinase (5μl containing 2000 units/ml) were added to the solution, which was then allowed to stand at room temperature for 15 minutes. 'Darco-G-60' (Registered Trade Mark) (10 mg) was added to each tube and the contents mixed periodically for 10 minutes. The charcoal was removed through a 'Millipore AP 250 2200' (Registered Trade Mark) filter and the filter was washed with three 10 ml portions of cold water. The charcoal and the filter were then radioactively counted.

The radioactive count from the contents of tubes 2 and 3 was taken as the maximum count, since these tubes contained no test compound and thus gave 0% enzyme inhibition. The percentage inhibition produced by the contents of the remaining tubes could then be calculated by relating their radioactive count to the maximum, as determined above.

The contents of tubes 10 to 12 were chromatographically analysed as described under part (b), and used as controls, tubes 10 and 11 containing no test compound (and hence giving 0% inhibition) being accorded the value of 100%. The percentage inhibition exhibited by the contents of the tubes in part (b) of the experiment could then be calculated in relation to this, by comparing the respective chromatograms. (b) The activity of the test compound of formula (I) against 'synthetase' was determined as follows, by monitoring the formation of dihydropteroate $C^{14}$.

A pool of Pt was prepared from ATP neutralised (50μl, 0.1M), $MgCl_2.6H_2O$(50μl,0.1M), dithiothreitol (100μl,0.1M), tris buffer (100μl,0.4M,pH 8.3), HMPL (25μl,876μM) and 170μl of a solution containing HMPPS. The mixture was incubated for 60 minutes at 37° C, chilled briefly on ice and then dextrose (100μl containing 72.1mg/ml) and hexokinase (20μl containing 2000 units/ml) were added at room temperature to the solution, which was allowed to stand at this temperature for 15 minutes.

A solution of $MgCl_2.6H_2O$ (10μl,0.1M), pAB-$C^{14}$ (10μl,0.4mM), dithiothreitol (20μl,0.1M) and tris buffer (20μl,0.4M,pH8.3) was made in each of five test tubes and then 80μl of the contents of the pool added to each, together with synthetase and/or test compound of formula (I) as indicated in Table 2. The solution was then made up to 200μl with distilled water.

Two control test tubes were prepared, each containing ATP (10μl,0.1M), $MgCl_2.6H_2O$(10μl,0.1M), dithiothreitol (20μl,0.1M) tris buffer (20μl,0.4M,pH 8.3), pAB-$C^{14}$(10μl, 0.4mM), and 20μl of a solution containing HMPPS and 'synthetase' of known activity. The test compound was added to the second of these two tubes up to a final concentration of $10^{-5}$M, and both tubes were made up with distilled water to 200μl.

All seven tubes were then incubated for 30 minutes at 37° C, chilled on ice and then these, together with control tubes 10 to 12 from part (a), were chromatographically analysed as follows.

100μl of the contents of each of the tubes was spotted onto Whatman no. 3MM chromatography paper (2×20 cm) at the 'origin', the run descending in a Sorenson buffer of potassium and sodium phosphates (0.1M,pH 7.0) for 10 to 15 cm. From the relative positions of the spots obtained from the contents of the different tubes, the various percentage inhibitions of synthetase could be evaluated by reference to control tubes 10 and 11, which gave 0% inhibition.

Those compounds which, as result of these tests, were found to give 50% inhibition at a concentration of 100μM or less, are those which exert a useful potentiating effect, and subject to their toxicity being favourable, may be included in the compositions described in this specification.

2-Amino-4-hydroxy-6-bromomethyl, 7,7-dimethyl-7,8-dihydropteridine and the 6-dibromomethyl analogue were found to give 50% inhibition at concentrations of 5μM and 25μM respectively.

EXAMPLE 6

Tablet Formulation

| | |
|---|---|
| Compound of formula (I) ($R=CH_2Br$)$R^1=R^2=Me$) (pure) | 100 mg |
| Trimethoprim (pure) | 25 mg |
| Sulfaguanidine (B.P.C.) | 100 mg. |
| + cornstarch, lactose gelatin, talcum and magnesium stearate | |

Preparation — the above constituents were mixed together using known methods of pharmacy to form a granulation which was then compressed into tablets.

EXAMPLE 7

Tablet Formulation

| | |
|---|---|
| "Pyremathimine" (Pyrimethamine) B.P. | 15 mg |
| Compound of formula (I)($R=CH_2Br;R^1=R^2=Me$) (pure) | 150 mg |
| which was then prepared to form a tablet as in Example E. | |

EXAMPLE 8

Tablet Formulation

| | |
|---|---|
| Sulfanilamide B.P.C. | 150 mg |
| Compound of formula (I)($R=CH_2Br_2;R^1=R^2=Me$) (pure) | 175 mg |
| which was then prepared to form a tablet as in Example E. | |

EXAMPLE 9

Capsule Formulation

| | |
|---|---|
| Trimethoprim (pure) | 20 mg |
| Compound of formula (I)(R=CH$_2$Br;R$^1$=R$^2$=Me) (pure) | 100 mg |

Preparation — The compounds in granular form were blended together with lactose, cornstarch and magnesium stearate. The powder was filled into a two-piece, hard shell gelatin capsule using a capsulating machine.

EXAMPLE 10

Irrigant Solution

| | |
|---|---|
| Compound of formula (I)(R=CH$_2$Br;R$^1$=R$^2$=Me) (pure) | 1 mg/ml |
| Trimethoprim (pure) | 0.2 mg/ml |
| Solvent | water |

EXAMPLE 11

Irrigant Solution

| | |
|---|---|
| Compound of formula (I)(R=CHBr$_2$;R$^1$=R$^2$=Me) (pure) | 2 mg/ml |
| α-amino-2-toluenesulphonamide (pure) | 2 mg/ml |

EXAMPLE 12

Solution

| | |
|---|---|
| Compound of formula (I) (R=CH$_2$Br;R$^1$=R$^2$=Me) (pure) | 1.5 mg/ml |
| Diaveridine B. Vet C | 0.5 mg/ml |
| Kelfizine | 1.0 mg/ml |
| Solvent | Water |

EXAMPLE 13

Tablet Formulation

| | |
|---|---|
| Compound of formula (I) (R=CH$_2$Br;R$^1$=R$^2$=Me) (pure) | 500 mg |
| Microcrystalline-cellulose | 100 mg |
| Starch | 40 mg |
| Magnesium stearate | 10 mg |
| Methylhydroxyethylcellulose | 3 mg |
| | 653 mg |

The pteridine (I), microcrystalline cellulose and starch were granulated with a solution of the methylhydroxyethylcellulose in 50% aqueous ethyl alcohol. The magnesium stearate was added to the dried granules, and the whole then compressed.

TABLE 1.

| Tube No. | I | II | III | IV | V | VI | VII | VIII final Concn. | IX |
|---|---|---|---|---|---|---|---|---|---|
| 1 | — | 100μl | 15μl | — | 10μl | — | — | — | — |
| 2 | 5μl | " | " | — | " | — | — | — | — |
| 3 | " | " | " | — | " | — | — | — | — |
| 4 | " | " | " | — | " | — | — | 2.5×10$^{-6}$M | — |
| 5 | " | " | " | — | " | — | — | " | — |
| 6 | " | " | " | — | " | — | — | 1.0×10$^{-5}$M | — |
| 7 | " | " | " | — | " | — | — | " | — |
| 8 | " | " | " | — | " | — | — | 9.3×$_{"}$ $^{-5}$M | — |
| 9 | " | " | " | — | " | — | — | " | — |
| Controls | | | | | | | | | |
| 10 | — | — | — | 10μl | — | 10μl | 20μl | | 10μl |
| 11 | 5μl | — | — | " | — | " | " | | " |
| 12 | " | — | — | " | — | " | " | 1.0×10$^{-5}$M | " |

TABLE 2

| Tube No. | Excess Synthetase | Test compound Final Concentration. |
|---|---|---|
| 1 | — | — |
| 2 | + | — |
| 3 | + | 8.7 × 10$^{-6}$M |
| 4 | + | 1.0 × 10$^{-5}$M |
| 5 | + | 2.5 × 10$^{-6}$M |
| Controls | | |
| 6 | — | — |
| 7 | — | 1.0 × 10$^{-5}$M |

What we claim is:

1. A pharmaceutical composition for treating bacterial or protozoal infections comprising a compound of Formula (I), a tautomer form thereof or a pharmaceutically acceptable salt of the compound or its tautomer

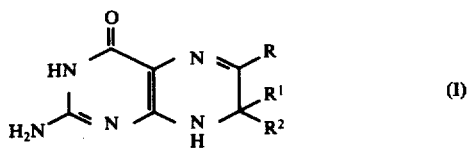

in an amount effective for treating bacterial or protozoal infections and a pharmaceutically acceptable carrier therefore where R is a lower alkyl group substituted with one or more halogen atoms, and R$^1$ and R$^2$ are the same or different and each is a lower alkyl group or R$^1$ and R$^2$, together with the carbon atom in the pteridine ring structure, form a spirocycloalkyl ring system having 4 to 6 carbon atoms outside the pteridine ring structure.

2. The composition of claim 1 wherein R is lower alkyl group substituted on the carbon atom adjacent the pteridine ring structure.

3. The composition of claim 1 wherein R is a lower alkyl group substituted with one or two halogen atoms.

4. The composition of claim 3 wherein the halogen atoms are bromine atoms.

5. The composition of claim 1 wherein R is a substituted methyl group.

6. The composition of claim 1 wherein R$^1$ and R$^2$ are lower alkyl groups.

7. The composition of claim 6 wherein the alkyl groups are the same and are methyl groups.

8. The composition of claim 1 in which R$^1$ and R$^2$ together with the carbon atom in the pteridine ring structure, form a spirocycloalkyl ring system having 4 to 6 carbon atoms outside the pteridine ring structure.

9. The composition of claim 1 wherein the compound is a salt of an acid or a base selected from the group consisting of hydrobromic acid, sulphuric acid, acetic acid, citric acid, tartaric acid, lactic acid, maleic acid, salicylic acid, sodium hydroxide, potassium hydroxide, tetramethyl ammonium hydroxide and ammonia.

10. The composition of claim 9 wherein the salt is the hydrochloric acid addition salt.

11. The composition of claim 1 in which the compound is selected from the group consisting of 2-amino-4-hydroxy-6-bromomethyl-7,7-dimethyl-7,8-dihydropteridine and 2-amino-4-hydroxy-6-dibromomethyl-7,7-dimethyl-7,8-dihydropteridine.

12. The composition of claim 1 in which the compound is 2-amino-4-hydroxy-6-bromomethyl-7,7-dimethyl-7,8-dihydropteridine or a tautomer thereof.

13. The composition of claim 1 in which the compound is 2-amino-4-hydroxy-6-dibromomethyl-7,7-dimethyl-7,8-dihydropteridine or a tautomer thereof.

14. The method of treating bacterial or protozoal infections in a mammal or bird comprising the administration to said mammal or bird the composition of claim 1 in an amount effective for treating bacterial or protozoal infections.

15. The method of claim 14 in which the compound is 2-amino-4-hydroxy-6-bromomethyl-7,7-dimethyl-7,8-dihydropteridine.

16. The method of claim 14 in which the compound is 2-amino-4-hydroxy-6-dibromomethyl-7,7-dimethyl-7,8-dihydropteridine.

* * * * *